United States Patent [19]

Sanfilippo et al.

[11] 4,112,007

[45] Sep. 5, 1978

[54] SELECTIVE HYDROGENATION IN GASEOUS PHASE OF CYCLOPENTADIENE OR A MIXTURE OF ETHYLENE AND ACETYLENE USING A PALLADIUM ZINC CATALYST DEACTIVATED WITH AMMONIA, AMMONIUM CHLORIDE, STEAM, OR THEIR MIXTURES

[75] Inventors: Domenico Sanfilippo, Milan; Morello Morelli, San Donato Milanese (Milan), both of Italy

[73] Assignee: ANIC S.p.A., Palermo, Italy

[21] Appl. No.: 688,836

[22] Filed: May 21, 1976

[30] Foreign Application Priority Data

May 23, 1975 [IT] Italy ............................. 23666 A/75

[51] Int. Cl.[2] ........................... C07C 5/06; C07C 5/08
[52] U.S. Cl. ........................... 260/666 A; 260/677 H; 260/683.9
[58] Field of Search ............ 260/666 A, 677 H, 683.9

[56] References Cited

U.S. PATENT DOCUMENTS

| 3,022,359 | 2/1962 | Wiese et al. | 260/666 A |
| 3,751,497 | 8/1973 | Schwerdtel et al. | 260/666 A |
| 3,819,734 | 6/1974 | Kothari et al. | 260/666 A |
| 3,900,526 | 8/1975 | Johnson | 260/681.5 |

FOREIGN PATENT DOCUMENTS 1,181,700  11/1964  Fed. Rep. of Germany ...... 260/666 A

*Primary Examiner*—Veronica O'Keefe
*Attorney, Agent, or Firm*—Morgan, Finnegan, Pine, Foley & Lee

[57] ABSTRACT

In a process for the selective hydrogenation of polyunsaturated compounds, by means of a catalyst system, the hydrogenation is carried out in gaseous phase in the presence of a catalyst of a metal of the eight group of the Periodical Table, partially deactivated by a deactivating system.

8 Claims, No Drawings

SELECTIVE HYDROGENATION IN GASEOUS PHASE OF CYCLOPENTADIENE OR A MIXTURE OF ETHYLENE AND ACETYLENE USING A PALLADIUM ZINC CATALYST DEACTIVATED WITH AMMONIA, AMMONIUM CHLORIDE, STEAM, OR THEIR MIXTURES

The present invention relates to a process for the selective hydrogenation in the gaseous phase of polyunsaturated compounds as such or in admixture with other hydrocarbons. Particularly, the present invention relates to the use of the catalysts for the selective hydrogenation based on an element of the group VIII, preferably Pd, and deactivated by inhibitors, which can be either supported or continuously fed.

By polyunsaturated compounds, those containing an unsaturation of acetylenic or olefinic type are meant.

According to the up to date art, Pd based catalysts and more generally catalysts based on metals of the eight group of the Periodic Table of the Elements are used in the selective hydrogenation in liquid phase of acetylene or polyolefine compounds. In this case valuable levels of the selectivity as monoolefins are obtained both by limiting the proportion of the hydrogen which is fed and by partially deactivating the catalyst through the impregnation or co-precipitation of a heavy metal salt. Such a salt, besides being possibly previously added on the catalyst, can also be continuously fed during the reaction by means of a solution formed by a suitable solvent. The presence of additional deactivating substances, such as ammonia or amines, is not compulsory.

In some cases it would be advantageous to operate in gaseous phase due to the greater simplicity of the operations, the lower cost of the equipment and the higher yields, especially in the case of the conjugated olefines in which the high concentrations of these compounds in the liquid phase causes relevant amounts of by-products to be formed to the detriment of the yield and of the catalyst life.

In this case, by using catalysts of metals of the Eighth group of the Periodic Table of Elements, it would be absolutely necessary to limit the H$_2$/polyunsaturated ratio, in order to maintain a fairly good selectivity at sufficiently high conversion rates.

It has now been found, which is the subject of the present invention, that it is possible to carry out the selective hydrogenation in gaseous phase of polyunsaturated compounds with high selectivity and with conversion rates up to 100%, by operating also in hydrogen excess, with catalysts based on elements of the Eighth group of the Periodic Table of Elements, preferably Pd, deactivated with cations of a heavy metal.

Better results are obtained by operating also in the simultaneous presence of at least a compound selected in the following classes and preferably more than one compound:
1. basic compounds, such as ammonia and amines
2. steam
3. quaternary ammonium salts The member of the eight group of the Periodic Table, and particularly the Pd, can be deposited onto a suitable substrate, such as for instance Al$_2$O$_3$, carbon, CaCO$_3$, BaSO$_4$, both in form of pellets and in powdery form with concentrations of between 0.01 and 5% by weight, preferably between 0.01 and 0.5. The heavy metal to be deposited onto the catalyst, selected amongst Zn, Pb, Hg, Cd, Sn, Cu, Fe, etc., can be used in form of compounds in which the anion is practically negligible, it being possible to use chlorides, nitrates, sulphates, acetates, oxalates, citrates, hydrates, etc.

The concentration of the heavy metal on the catalyst broadly varies and is comprised between 0.01 and 30% by weight, preferably between 0.1 and 5%.

As already mentioned, according to the process of the present invention, it is also possible to have simultaneously present steam and/or a basic compound and/or a quaternary ammonium salt. The best results are obtained when all these classes of compounds are simultaneously present.

The basic compound can be represented by the following formula

in which R$_1$, R$_2$, R$_3$, identical or different from each other, can be hydrogen or alkyl, allyl, cycloalkyl radicals containing up to 10 carbon atoms. The concentrations of steam and of the basic compound in the gas phase are broadly variable and the selectivity can be influenced thereby.

The quaternary ammonium compound, particularly a chloride, can be previously added to the catalyst or continuously fed during the reaction. Such a compound is of the type $(NR_4^+)_n X^{n-}$, wherein the R groups represent hydrogen or alkyl groups, either identical or different from each other, and X is an anion, preferably a halogen, and n is the number of negative charges of the anion. The temperature and the total pressure are not critical with respect to the selectivity, it being possible to advantageously operate in the range of 20° to 300° C and at a total pressure either atmospherical or higher. The deactivating substances employed can influence the selectivity or even, in some cases, show a beneficial effect on the catalyst life.

For a better understanding of the present invention, there are given some Examples, having explanatory but not limitative purpose.

EXAMPLE 1

100 parts of a catalyst comprising 0.3% of Pd on Al$_2$O$_3$, in form of pellets, are treated, by boiling for 2 hours, with 200 mls of a 15% Zn (CH$_3$COO)$_2$.H$_2$O aqueous solution. After filtration and drying, the catalyst contains 2.24% by weight of Zn. 75 g of this catalyst are charged in a jacketed reactor (internal diameter: 1.5 cms; height: 38 cms:). 30 to 60 standard liters/hour of H$_2$ and 27 to 55 standard liters/hour of cyclopentadiene (CPD) are fed on the catalyst. The following results have been obtained:

| H$_2$/CPD | 0.92 | 1.02 | 1.1 | 1.2 | 1.65 |
|---|---|---|---|---|---|
| Conversion % | 80 | 90 | 95 | 97.5 | 100 |
| Selectivity % | 90 | 87 | 84 | 81 | 35 |
| Yield % | 72 | 78.3 | 79.8 | 79 | 35 |

EXAMPLE 2

According to the conditions of the Example 1, 50 to 60 standard liters/hour of H$_2$ and 20-27 standard liters/hour of cyclopentadiene are fed to the reactor, together with 0.5 standard liters/hour of gaseous NH₃, the following results being thus obtained:

| $H_2$ | | | | | | |
|---|---|---|---|---|---|---|
| Conversion % | 1.8 | 1.85 | 2.05 | 2.39 | 2.45 | 2.70 |
| C% | 80 | 90 | 95 | 97.5 | 99 | 99.5 |
| Selectivity % | 97 | 96 | 95 | 93 | 90 | 86 |
| Yield % | 77.6 | 86.4 | 90.2 | 90.6 | 89 | 85.6 |

EXAMPLE 3

Likewise the method of the Example 1, a catalyst is prepared containing 0.94% Zn.

50 standard liters/hour $H_2$ and 38–46 standard liters/hour of cyclopentadiene, and furthermore 37 standard liters/hour of steam are fed on the catalyst, the following results being thus obtained:

| $H_2$ | | | | |
|---|---|---|---|---|
| CPD | 1.08 | 1.15 | 1.23 | 1.3 |
| Conversion % | 90 | 95 | 97.5 | 99.5 |
| Selectivity % | 93.5 | 91.5 | 89.5 | 78.5 |
| Yield % | 84 | 87 | 87.3 | 78 |

EXAMPLE 4

50 standard liters/hour $H_2$, 39–49 standard liters/hour of cyclopentadiene, 40 standard liters/hour of steam and 1 standard liter/hour of gaseous $NH_3$ are fed on the catalyst of the Example 3.

The following results are obtained:

| $H_2$ | | | | |
|---|---|---|---|---|
| CPD | 1.02 | 1.08 | 1.15 | 1.27 |
| Conversion % | 95 | 97.5 | 99.5 | 100 |
| Selectivity % | 94 | 92 | 86 | 75.3 |
| Yield % | 89.3 | 89.7 | 85.6 | 75.3 |

EXAMPLE 5

100 g of catalyst consisting of 0.3% Pd onto $Al_2O_3$ in form of pellets are treated, by boiling for two hours, with 200 mls of an aqueous solution containing 5% by weight of $Zn(CH_3COO)_2 \cdot 2H_2O$ and 3% by weight of $NH_4Cl$.

After filtration and drying, the catalyst contains 0.9% by weight Zn and 1.1% of ammonium salt (0.73% Cl).

50 standard liters/hour $H_2$ and 27–30 standard liters/hour of cyclopentadiene are fed on such a catalyst, the following results being obtained:

| $H_2$ | | | |
|---|---|---|---|
| CPD | 1.68 | 1.76 | 1.84 |
| Conversion % | 95 | 97.5 | 99.8 |
| Selectivity % | 94.5 | 93 | 80 |
| Yield % | 89.7 | 90.6 | 79.8 |

EXAMPLE 6

50 standard liters/hour $H_2$ and 27 standard liters/hour of cyclopentadiene, with a ratio $H_2/CPD = 1.84$ and 1 liter/hour of $NH_3$ gas are fed on a catalyst like that of the Example 5, thus obtaining a 100% conversion and a selectivity of 90%, the yield being 90%.

EXAMPLE 7

50 standard liters/hour $H_2$, 27 standard liters/hour CPD and 37 standard liters/hour of steam are fed on a catalyst like that of the Example 5, there being obtained a 93% selectivity, a 99.5% conversion, the yields being 92.5%.

EXAMPLE 8

50 standard liters/hour $H_2$, 24–49 standard liters/hour of cyclopentadiene, 37 standard liters/hour of steam, 1.8 standard liters/hour $NH_3$ gas are fed on a catalyst like that of the Example 5, the following results being obtained:

| $H_2$ | | | | | | |
|---|---|---|---|---|---|---|
| CPD | 1.02 | 1.05 | 1.06 | 1.08 | 1.15 | 2.04 |
| Conversion % | 90 | 95 | 97.5 | 99.5 | 100 | 100 |
| Selectivity % | 98.9 | 98.5 | 98 | 97.4 | 97.2 | 93 |
| Yield % | 89 | 93.6 | 95.5 | 97 | 97.2 | 93 |

EXAMPLE 9

50 standard liters/hour of ethylene, containing 1% $C_2H_2$ and variable amounts of hydrogen, are fed on a 0.04% Pd on $Al_2O_3$ catalyst, in form of pellets, the catalyst also containing 1.1% Zn. The following results are obtained:

| $H_2$ | | | | | | | | | | |
|---|---|---|---|---|---|---|---|---|---|---|
| $C_2H_2$ | 1.2 | 1.3 | 1.4 | 2.1 | 2.2 | 2.3 | 3.3 | 9 | 9.7 | 10.5 |
| T° C | 121 | 121 | 121 | 65 | 65 | 150 | 121 | 65 | 150 | 120 |
| ppm $C_2H_2$ res. | 148 | 12 | 5 | 34 | 7 | 2 | 0 | 0 | 0 | 0 |
| $C_2H_6$% form. | 0.17 | 0.31 | 0.42 | 0.45 | 0.49 | 1.25 | 2.3 | 6.4 | 8.7 | 9.5 |

EXAMPLE 10

50 standard liters/hour of ethylene, containing 1% $C_2H_2$; 0.8 standard liters/hour of steam, 2 standard liters/hour of gaseous $NH_3$ and $H_2$ in variable ratios are fed on a 0.04% Pd on $Al_2O_3$ catalyst, in form of pellets, the catalyst also containing 1.17% Zn. The following results are obtained:

| $H_2$ | | | | | | | | | |
|---|---|---|---|---|---|---|---|---|---|
| $C_2H_2$ | 1 | 1.1 | 1.2 | 1.4 | 2.8 | 2.9 | 9 | 9 | 9 |
| T° C | 120 | 120 | 120 | 150 | 63 | 63 | 63 | 125 | 150 |
| ppm $C_2H_2$ res. | 40 | 2 | 0 | 2 | 22 | 2 | 0 | 0 | 0 |
| $C_2H_6$% | 0.08 | 0.1 | 0.15 | 0.4 | 0.29 | 0.38 | 2.47 | 6.35 | 7.6 |

| | | | | | | | |
|---|---|---|---|---|---|---|---|
| $\dfrac{H_2}{\text{form.}}$ | | | | | | | |

EXAMPLE 11

50 standard liters/hour of ethylene, containing 1% $C_2H_2$, 0.8 standard liters/hour of steam, 2 standard liters/hour of gaseous $NH_3$ and $H_2$ in variable ratios are fed on a 0.04% Pd on $Al_2O_3$ catalyst, in form of pellets, the catalyst also containing 0.15% Zn and 1.18% $NH_4Cl$. The following results are obtained:

| $\dfrac{H_2}{C_2H_2}$ | 1.1 | 1.2 | 1.5 | 4.8 | 8.7 | 8.8 | 9 |
|---|---|---|---|---|---|---|---|
| T° C | 155 | 155 | 120 | 62 | 155 | 120 | 69 |
| $C_2H_2$ res. ppm | 14 | 9 | 2 | 14 | 0 | 0 | 0 |
| $C_2H_6$ % form. | 0.06 | 0.06 | 0.15 | 0.26 | 2.9 | 3 | 1.38 |

We claim:

1. A process for the selective hydrogenation of a polyunsaturated hydrocarbon which comprises contacting a hydrocarbon selected from the group consisting of cyclopentadiene and a mixture of ethylene and acetylene with hydrogen in the gaseous state in the presence of a catalyst consisting essentially of palladium and a zinc salt and a further deactivating substance selected from the group consisting of ammonia, ammonium chloride and steam and mixtures thereof, said process being carried out at a temperature of between 20° C. and 300° C. and an absolute pressure of between 1 and 20 atmospheres.

2. The process of claim 1 wherein the deactivating substance is ammonia.

3. The process of claim 1 wherein the deactivating substance is ammonium chloride.

4. The process of claim 1 wherein the deactivating substance is steam.

5. The process of claim 1 wherein the deactivating substance is steam and ammonia.

6. The process of claim 1 wherein the deactivating substance is steam, ammonia and ammonium chloride.

7. The process of claim 1 wherein the deactivating substance is ammonia and ammonium chloride.

8. The process of claim 1 wherein the deactivating substance is steam and ammonium chloide.

* * * * *